(12) United States Patent
Yamaguchi et al.

(10) Patent No.: US 7,500,754 B2
(45) Date of Patent: Mar. 10, 2009

(54) OPHTHALMOLOGIC IMAGING APPARATUS

(75) Inventors: Tatsuo Yamaguchi, Tokyo (JP); Toshifumi Mihashi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 136 days.

(21) Appl. No.: 11/797,124

(22) Filed: May 1, 2007

(65) Prior Publication Data

US 2007/0258045 A1    Nov. 8, 2007

(30) Foreign Application Priority Data

May 2, 2006    (JP) .............................. 2006-128117

(51) Int. Cl.
*A61B 3/10* (2006.01)
*A61B 3/14* (2006.01)
(52) U.S. Cl. ................ 351/221; 351/206; 351/215
(58) Field of Classification Search ............... 351/205, 351/206, 215, 221
See application file for complete search history.

(56) References Cited

U.S. PATENT DOCUMENTS 5,430,507 A * 7/1995 Nishio et al. .............. 351/208

2005/0286018 A1    12/2005 Yamaguchi et al.
2007/0030447 A1    2/2007 Yamaguchi et al.

FOREIGN PATENT DOCUMENTS

| JP | 2004-113405 | 4/2004 |
|---|---|---|
| JP | 2004-159779 | 6/2004 |
| JP | 2004-159784 | 6/2004 |
| JP | 2004-329282 | 11/2004 |
| JP | 2006-006362 | 1/2006 |

* cited by examiner

*Primary Examiner*—William C Choi
(74) *Attorney, Agent, or Firm*—Foley & Lardner LLP

(57) ABSTRACT

Light from a light source is divided into S-polarization and P-polarization light. The P-polarization light is incident to a retinal illumination system for high-power image and the S-polarization light is incident to a retinal illumination system for low-power image. These lights are set center illumination and ring illumination by aperture diaphragms. Reflection light flux from a cornea under the high-power retina illumination light passes through the center of a perforated mirror, and thus light reflected from the retina and the perforated mirror is received through a high-power optical system to achieve an excellent retinal image having no flare. Likewise, reflection light flux from the cornea under the low-power retina illumination light is reflected from the perforated mirror, and thus light reflected from the retina and passing through the center of the hole is received through a low-power optical system to achieve an excellent retinal image having no flare.

6 Claims, 8 Drawing Sheets

FOR OBSERVATION OF CELL

FOR OBSERVATION OF LEUCOCYTE

FOR OBSERVATION OF BLOOD VESSEL

OPHTHALMOLOGIC IMAGING APPARATUS

CROSS REFERENCE TO RELATED APPLICATION

This application claims priority from Japanese Patent Application 2006-128117, filed May 2, 2006, all of which are incorporated herein by reference in their entirety.

BACKGROUND OF THE INVENTION

1. Field of the Invention

The present invention relates to an ophthalmologic imaging apparatus, and particularly to an ophthalmologic imaging apparatus that can pick up both a high-power retinal image and a low-power retinal image at the same time.

2. Description of the Related Art

The following technologies have been disclosed by the assignee of present application. An eye-characteristic measurement apparatus which compensates for aberrations of an eye under measurement by a compensation optical section and measures precisely a minute aberration remaining after compensation is disclosed, for example, in Japanese Unexamined Patent Application Publication No. 2004-113405, No. 2004-159779, and No. 2004-159784. A retina observation apparatus which compensates a light beam reflected by an eye under measurement in order to improve retinal image quality and obtains an optimal image is disclosed, for example, in Japanese Unexamined Patent Application Publication No. 2004-329282. A retinal image observation apparatus which detects a displacement of an eye under measurement and moves a wavefront compensation device according to the detected shift position to compensate the wavefront is disclosed, for example, in Japanese Unexamined Patent Application Publication No. 2006-006362.

However, in conventional optical devices, when images based on a high-power system and a low-power system are achieved, light sources having different wavelengths are used, or optical systems are separately prepared and are switched by a mirror or the like. However, it has been hitherto difficult to achieve both the high-power image and the low-power image at the same time and with the same wavelength in these conventional optical devices. Furthermore, when conventional Adaptive Optics is applied to a retina camera, an image can be achieved with a high-resolution (high-power) with which cells can be observed, however, it would be very difficult to verify which site on the retina is measured because the magnifying power is excessively high.

SUMMARY OF THE INVENTION

The present invention has been implemented in view of the foregoing point, and has an object to provide an ophthalmologic imaging apparatus that can achieve both a low-power image and a high-power image at the same time. Furthermore, the present invention has an object to provide an ophthalmologic imaging apparatus that can specify the position of the high-power image on the basis of the low-power image, and specify the detailed position of causal agent. Still furthermore, the present invention has an object to achieve a desired observation target image by using polarization and a perforated mirror and designing the hole diameter of the perforated mirror in conformity with the size of a cell or blood vessel to be observed, for example.

According to the solving means of this invention, there is provided an ophthalmologic imaging apparatus comprising:

a light source section for emitting illumination light to illuminate a retina;

an illumination optical system for illuminating the retina of an eye under measurement by a first passage for passing a part of an illumination light flux from the light source section through a first aperture diaphragm having an opening formed at a center portion at a conjugate position with a pupil, and a second passage for passing a part of the illumination light flux from the light source section through a second aperture diaphragm having an opening formed on a periphery portion at a conjugate position with the pupil;

an aberration compensation section for applying compensation to a reflection light flux from the retina on the basis of measured aberrations so as to offset the aberrations;

an aberration measuring section for illuminating the eye under measurement, receiving a reflection light flux under the illumination from the eye under measurement through the aberration compensation section and measuring the aberrations of the reflection light flux;

an image pickup optical system including a reflection section that has an opening at a center portion at a conjugate position with the pupil, passes a light flux at the center portion and reflects the light flux at a peripheral portion, for achieving images of first and second magnifications of the retina of the eye under measurement by a third passage for achieving a retinal image of a first magnification by the reflection light flux which is from the retina and is compensated in aberrations in the aberration compensation section and is passed through the opening of the reflection section, and a fourth passage for achieving a retinal image of a second magnification by the reflection light flux which is from the retina and is compensated in aberrations in the aberration compensation section and is reflected from the peripheral portion around the opening of the reflection section;

a first light-receiving section for receiving the light flux passing through the third passage; and a second light-receiving section for receiving the light flux passing through the fourth passage, and images of different magnifications being achieved by the first light-receiving section and the second light-receiving section.

According to the present invention, it can provide an ophthalmologic imaging apparatus that can achieve both a low-power image and a high-power image at the same time. Furthermore, according to the present invention, it can provide an ophthalmologic imaging apparatus that can specify the position of the high-power image on the basis of the low-power image, and specify the detailed position of causal agent. Still furthermore, according to the present invention, it can achieve a desired observation target image by using polarization and a perforated mirror and designing the hole diameter of the perforated mirror in conformity with the size of a cell or blood vessel to be observed, for example.

DETAILED DESCRIPTION OF THE PREFERRED EMBODIMENTS

1. Outline

This embodiment relates to an Adaptive Optics retina camera characterized in that a high-power (high magnifying power) retinal image and a low-power (low magnifying power) retinal image can be picked up at the same time. This embodiment can simultaneously achieve an image from the Adaptive Optics system which can observe retina with high resolution and an image from a finder system which can acquire an image with wide range by using polarization and pupil division. In this embodiment, the high power (high magnifying power) and the low-power (low magnifying power) are relative magnifying powers, and represent different two magnifying powers (first magnifying power and second magnifying power). For example, the low power may be set to a magnifying power for achieving an image of the overall retina, and the high power may be set to a magnifying power for achieving an image of a local position of the retina, however, they are not limited.

2. Optical Arrangement

Figure 1:
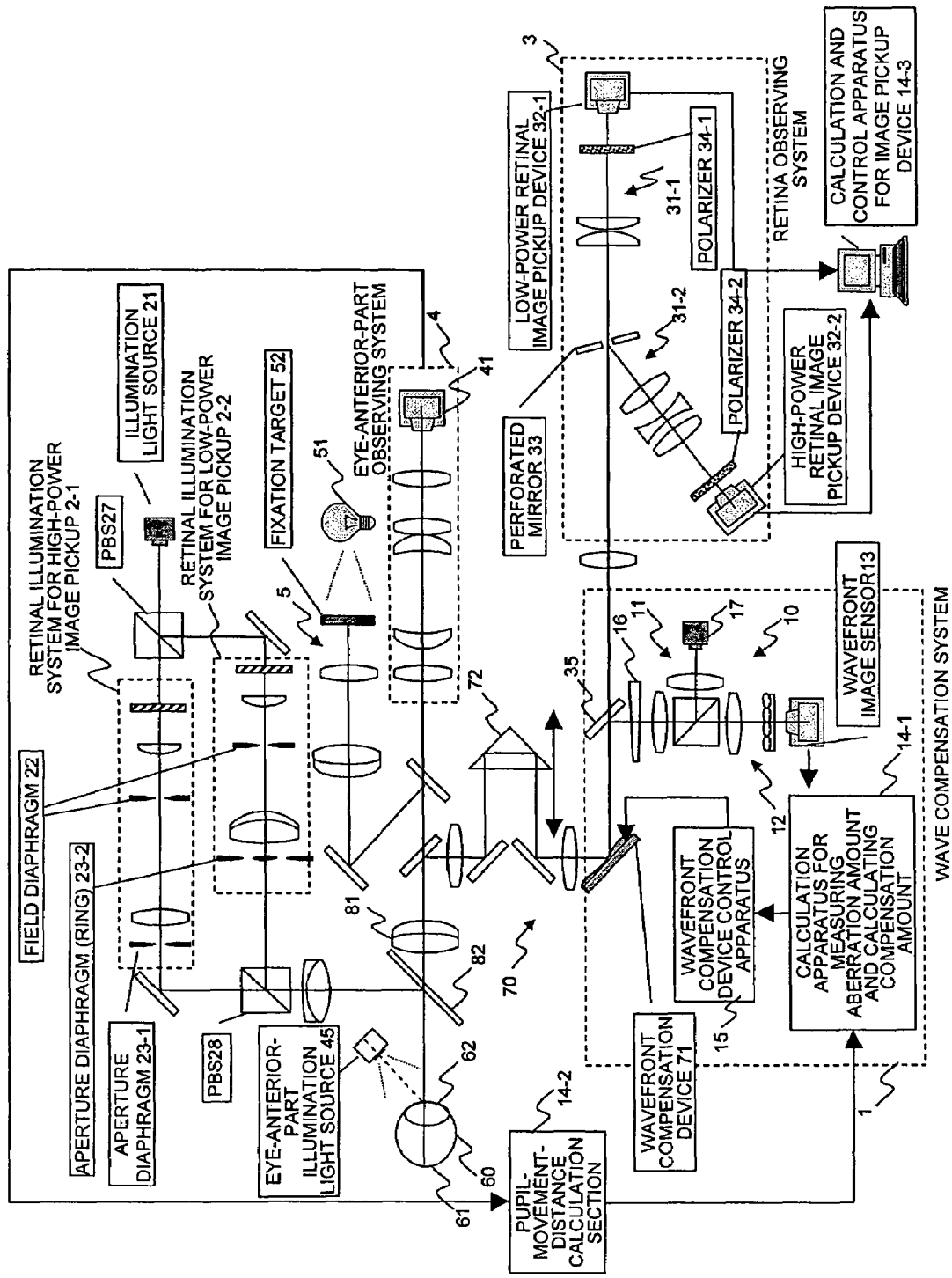
FIG. 1 is a diagram showing an optical arrangement according to an embodiment.

FIG. 1 shows a diagram showing the optical arrangement of the ophthalmologic imaging apparatus.

The retina observing apparatus (ophthalmologic imaging apparatus) comprises a wavefront-compensation system 1, a retinal illumination system for high-power image pickup 2-1, a retinal illumination system for low-power image pickup 2-2, a retina observing system 3, an eye-anterior-part observation system 4, an eye-anterior-part illumination light source 45, a fixation system 5, a compensation optical section 70, a pupil-movement-distance calculation section 14-2, an image pickup device calculating/controlling device (retinal image generation section) 14-3, a second light source section (illumination light source) 21, and polarization beam splitters (hereinafter referred to as "PBS") 27 and 28.

The wavefront compensation system (aberration compensation section) 1 includes a first illumination optical system 11, a first light-receiving optical system 12, a wavefront measurement system 10 having a point image light-receiving section 13, an aberration-measurement and compensation-computation calculation apparatus (aberration calculation section, hereinafter called a calculation apparatus) 14-1, and a wavefront-compensation-device control apparatus 15. The calculation section 14-1, the pupil-movement-distance calculation section 14-2, and the fundus-image generation section 14-3 can, for example, be provided for one arithmetic section or a plurality of arithmetic sections. In the figure, a retina (eyeground) 61 and a cornea (eye anterior part) 62 are shown in an eye under measurement 60.

The first illumination optical system (point-image projection optical system) 11 includes, for example, a first light source section (for example, a wavefront-measurement light source) 17, and illuminates a minute area (or a target) on the retina of the eye under measurement by a light beam emitted from the first light source section 17. The first illumination optical system 11 also includes, for example, a condenser lens and a relay lens.

It is preferred that the first light source section 17 has high spatial coherence and not-high temporal coherence. As an example, a super luminescence diode (SLD) is employed here as the first light source section 17, and serves as a point light source having high luminance. The first light source section 17 is not limited to an SLD, and may be a laser source, which has high spatial and temporal coherence, if the temporal coherence is appropriately reduced by inserting a rotary diffusing plate. The first light source section 17 may be an LED, which has not-high spatial and temporal coherence, if its quantity of light is sufficient and a pinhole is inserted on the optical path at the position of the light source. The first wavelength of the first light source section 17 used for illumination is, for example, a wavelength in an infrared region, such as 860 nm or 780 nm.

The first light-receiving optical system (point image light-receiving optical system) 12 receives light reflected by and returned from the retina and guides it to the point image light-receiving section (such as a wavefront image sensor) 13. The first light-receiving optical system includes a relay lens, a beam splitter, and a conversion member (a splitting device such as a Hartman plate) for converting the reflected light beam into at least 17 beams. The beam splitter is formed of a mirror (such as a polarization beam splitter) which reflects light emitted from the first light source section 17 and transmits the reflected light beam reflected by the retina of the eye under measurement 60 and returned through an afocal lens 81. The conversion member is a wavefront conversion member for converting the reflected light beam into a plurality of beams. A plurality of micro Fresnel lenses disposed on a plane perpendicular to the optical axis can be used as the conversion member. The light beam reflected from the retina 61 is condensed on the point image light-receiving section 13 through the conversion member.

The point image light-receiving section 13 receives light from the first light-receiving optical system 12, which is transmitted through the conversion member, and generates a first signal.

While the first illumination optical system 11 and the first light-receiving optical system 12 keep a relationship such that, assuming that light emitted from the first light source section 17 is reflected at a point where the light is condensed, the point image light-receiving section 13 has the maximum signal peak of the reflected light, a prism 72 can be moved in a direction in which the signal peak obtained by the point image light-receiving section 13 increases and stopped at a position where the signal peak reaches the maximum. As a result, the light emitted from the first light-source section 17 is condensed on the eye under measurement.

The retina illumination system for high-power image pickup 2-1 has a field diaphragm 22, an aperture diaphragm 23-1, and a condenser lens, for example. The retina illumination system for low-power image pickup 2-2 has a field diaphragm 22, an aperture diaphragm (ring) 23-2, and a condenser lens, for example. The aperture diaphragm 23-1 of the retina illumination system for high-power image pickup 2-1 and the aperture diaphragm 23-2 of the retina illumination system for low-power image pickup 2-2 are conjugated to the pupil.

A light source having low coherence such as a krypton lamp or the like is desirable as the second light source section (illumination light source) 21, however, even a light source having high coherence such as a laser diode, a gas laser or the like may be used while a diffusion plate or the like is rotated at high speed in the optical path. Furthermore, the wavelengths of the light sources such as a first light source 17, the eye-anterior-part illumination light source 45, etc. may be properly selected, for example, the wavelength of the first light source 17 for Hartmann measurement may be set to 840 nm, and the wavelength of the eye-anterior-part illumination light source 45 may be set in the range from 850 to 930 nm (actually, 860 to 880 nm, for example) which corresponds to the infrared or near-infrared region. As the beam splitter 82 may be used a beam splitter for reflecting a flux of light from the second light source section 21 and transmitting therethrough a flux of light reflecting and returning from a measurement target eye 60.

Each of PBSs 27 and 28 divides light from the illumination light source 21 into S-polarization light and P-polarization light. For example, PBSs 27 and 28 allocate P-polarization light to the retina illumination system for high-power image pickup 2-1 and allocate S-polarization light to the retina illumination system for low-power image pickup 2-2, and set center illumination and ring illumination for the retina illumination system for high-power image pickup 2-1 and the retina illumination system for low-power image pickup 2-2 by using the aperture diaphragms 23-1 and 23-2, respectively. The sizes of the aperture diaphragms 23-1 and 23-2 are set so that two light beams emitted from these aperture diaphragms 23-1 and 23-2 are not overlapped with each other when they are afterwards combined with each other.

As shown in FIG. 1, incident light is input from the inside of a pupil and a light intercepting plate (for example, a perforated mirror is used in FIG. 1) or the like is inserted at the conjugate point of a cornea and a crystal lens to cut noises of the cornea, etc. (harmful reflection). Furthermore, the aperture diaphragm 23-1 of the retina illumination system for high-power image pickup 2-1 and the aperture diaphragm 23-2 of the retina illumination system for low-power image pickup 2-2 are arranged in the neighborhood of the conjugate point with the pupil, thereby establishing an optical system in which noise light can be removed by a cornea reflection removing mirror 33 described later. The field diaphragm 22 is disposed at the conjugate point of the retina, and thus even when a cell or the like is observed, light can be applied to it by limiting the light application range, and the load imposed on a person being examined can be reduced.

The rotational diffusion plate reduces the speckle of the high coherence light source (for example, laser by rotating the diffusion plate at a high speed. It is desirable that the diffusion plate is rotated substantially at the rotational number of 10000 rpm or more as an example although it is dependent on the exposure time.

The retina observing system 3 has a high-power retina observing system 31-2, a low-power retina observing system 31-1, a high-power retinal image pickup device (second light-receiving section) 32-2, a low-power retinal image pickup device (first light-receiving section) 32-1, the cornea reflection removing mirror (perforated mirror) 33, an afocal lens 81 and a beam splitter 35.

For example, the high-power retina observing system 31-2 has a second polarizer 34-2, and a high-power condenser lens (optical system). The high-power retina observing system 31-2 leads to the high-power retinal image pickup device 32-2 light which is reflected from the retina 61 and compensated in aberration by a compensation optical section 70. The high-power retinal image pickup device 32-2 receives retinal image light formed by the high-power retina observing system 31-2 to generate a signal. The high-power retinal image pickup device 32-2 can be constructed by a light-receiving element having sensitivity to a second wavelength (for example, red light) from the illumination light source 21.

The low-power retina observing system 31-1 has a first polarizer 34-1 and a low-power condenser lens, for example. The low-power retina observing system 31-1 leads to the low-power retinal image pickup device 32-1 light which is reflected from the retina 61 and compensated in aberration by the compensation optical section 70. The low-power retinal image pickup device 32-1 receives a retinal image light formed by the low-power retina observing system 31-1, and generates a signal. The low-power retinal image pickup device 32-1 may be constructed by a light-receiving device having sensitivity to the second wavelength.

The cornea reflection removing mirror 33 is preferably used at a shallow angle in order to make the pupil conjugated. The beam splitter 35 is constructed by a dichroic mirror for reflecting a flux of light having a first wavelength therefrom and passing a flux of light having a second wavelength therethrough, for example. In this embodiment, it is assumed that the afocal lens 81, the beam splitter 35, etc. are provided to the retina observing system 3 for convenience's sake, however, they may be provided to the first light-receiving optical system 12. Furthermore, in the retina observing system 3, the cornea reflection removing mirror (perforated mirror) 33 is disposed so as to be conjugated with or nearly conjugated with the aperture diaphragms 23-1 and 23-2.

A flux of reflected light from the cornea of the high-power retina illumination light passes through the center of the cornea reflection removing mirror 33, and thus the light from the retina which is reflected from the cornea reflection removing mirror 33 provides an excellent image having no flare. Likewise, a flux of reflected light from the cornea of the low-power retina illumination light is reflected from the cornea reflection removing mirror 33, and thus the light from the retina which passes through the center of the hole provides an excellent image having no flare. The pupil-dividing high-power system may be the center of the cornea reflection removing mirror, however, it is better to use a system reflected from the cornea reflection removing mirror in consideration of the characteristic of the optical system.

The polarizers 34-1 and 34-2 are inserted so that the respective light beams of the high power retina observing system 31-2 and the low-power retina-observing system 31-1 are not incident. According to this embodiment, the second polarizer 34-2 is oriented in the high-power retina observing system 31-2, so that P-polarization light passes through the second polarizer 34-2, and the first polarizer 34-1 is oriented in the low-power retina observing system 31-1 so that S-polarization light passes through the first polarizer 34-1. Accordingly, both the light beams are prevented from exercising an influence.

Figure 8:
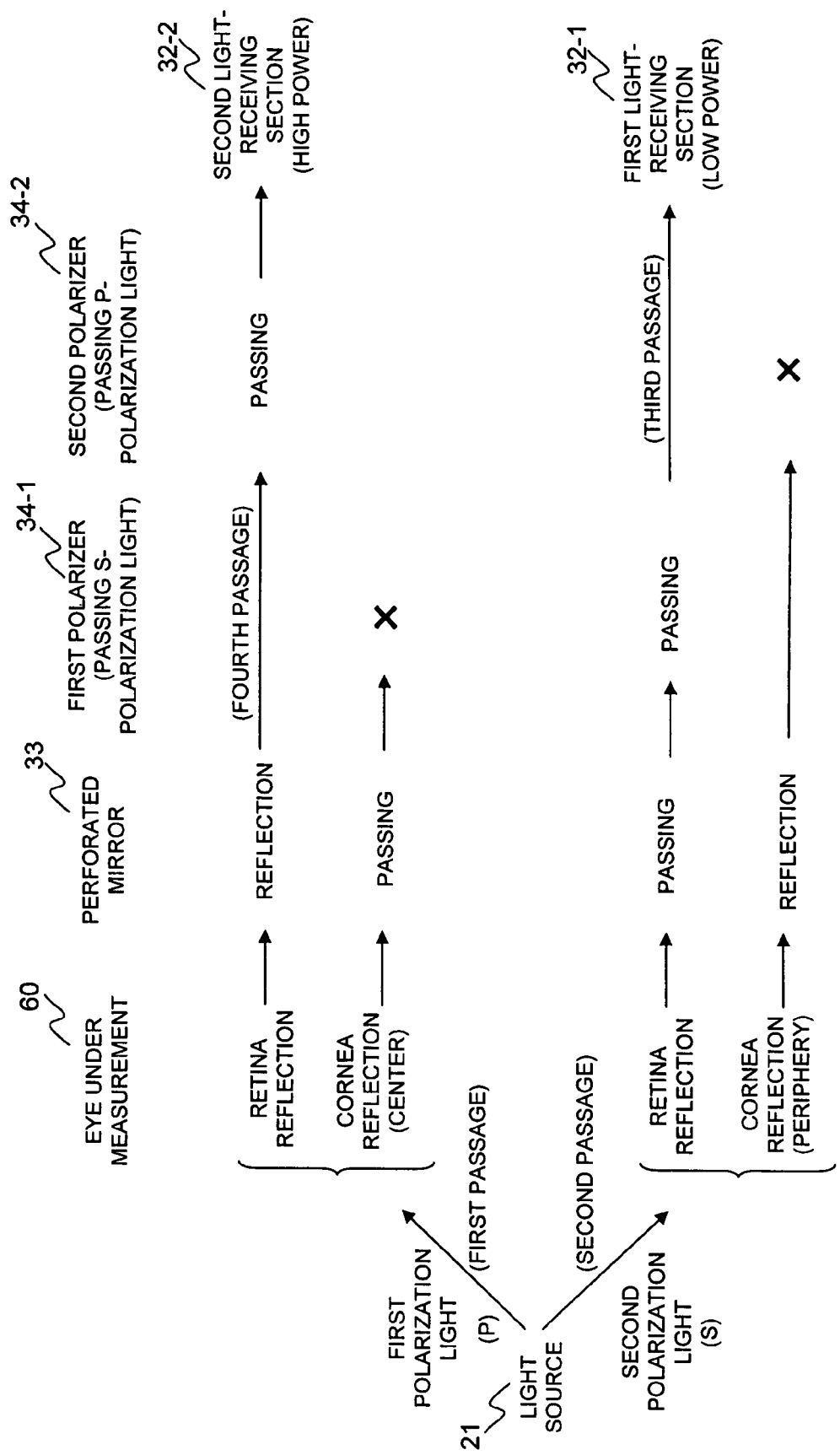
FIG. 8 is a diagram showing polarization light and reflection light flux.

FIG. 8 is a diagram showing polarization light and a flux of reflection light.

The splitting means (PBS) 27 and 28 divide a flux of illumination light from the light source section 21 into a light flux of first polarization light (P-polarization light) and a light flux of second polarization light (S-polarization light). Furthermore, they lead the light flux of the first polarization light to a first passage (retina illumination system for high-power image pickup 2-1), and leads the light flux of the second polarization light to a second passage (retina illumination system for low-power image pickup 2-2). The light flux of the first polarization light passes through the aperture diaphragm 23-1 which is conjugated with the pupil and opened at the center thereof, and reflects in the neighborhood of the pupil center at the cornea. Furthermore, it is also reflected from the retina. On the other hand, the light flux of the second polarization light passes through the aperture diaphragm 23-2 which is conjugated with the pupil and opened at the peripheral portion thereof, and reflects from the periphery around the pupil center at the cornea. It is also reflected from the retina.

The first polarizer 34-1 passes the light flux of the second polarization light out of the light flux containing the light flux of the first polarization light passing through the reflection portion (perforated mirror) 33 and reflected from the cornea and the light flux of the second polarization light reflected from the retina, and leads the reflection light flux from the retina to the light-receiving section 32-1. The second polarizer 34-2 passes the light flux of the first polarization light out of the light flux containing the light flux of the second polarization light which is reflected from the reflection section 33 and reflected from the cornea and the light flux of the first polarization light reflected from the retina, and leads the reflection light flux from the retina to the light-receiving section 32-2.

The compensation optical section (aberration compensation section) 70 has a wavefront compensation device 71 such as adaptive optical system (adaptive optics) for compensating measurement, light for aberration, the moving prism (diopter-adjustment prism) 72 for moving along the optical axis to compensate a spherical component and/or a spherical lens. The compensation optical section 70 is disposed in the first and second light-receiving optical systems 12, the high-power retina observing system 31-2 and the low-power retina observing system 31-1, and compensates, for example, for the aberration of a reflected light beam reflected by and returned from the eye under measurement 60. The compensation optical section 70 may compensate light emitted from the first light source 17 for aberration to illuminate a minute area on the retina of the eye under measurement by a light beam of which aberration has been compensated for.

The wavefront compensation device 71 can be a variable-shape mirror (a deformable mirror or a variable mirror) or a spatial light modulator such as liquid crystal. An appropriate optical system capable of compensating measurement light for aberration may also be used. A variable-shape mirror changes the reflection direction of light by deforming the mirror by an actuator provided inside the mirror. Other appropriate deforming methods can be used such as a deforming method using a capacitor or a piezoelectric device. A liquid-crystal spatial light modulator uses a liquid-crystal alignment characteristic to modulate a phase, and is used in reflection in many cases in the same way as the variable-shape mirror. When the liquid-crystal spatial light modulator is used, a polarizer is required in an optical path in some cases. The wavefront compensation device 71 may be a transmission-type optical system, in addition to a reflection-type optical system. The wavefront compensation device 71 compensates for aberration by, for example, being deformed according to the output of the wavefront-compensation-device control apparatus 15.

It is preferred that a parallel light beam is incident on the wavefront compensation device 71. Incident light is not limited to parallel light beams. When the eye under measurement 60 has no aberration, for example, light reflected from the retina of the eye under measurement 60 is incident on the wavefront compensation device 71 as a parallel light beam. Light emitted from the first light source section 17 is incident on the wavefront compensation device 71 as a parallel light beam.

The moving prism 72 is moved according to the output of the calculation apparatus 14-1. The moving prism 72 is driven, for example, by an appropriate driving section. A spherical component can be compensated for because the moving prism 72 is moved. The spherical component can be compensated for if a spherical lens is used, instead of moving the moving prism 72.

A motored stage that moves the wavefront compensation device 71 according to the output of a motor control circuit by following the pupil movement distance obtained by the pupil-movement-distance calculation section 14-2 can be further provided. For example, the motored stage moves the wavefront compensation device 71 in a direction traversing the optical axis or in a plane perpendicular to the normal line. With this, a point (such as the center) of the wavefront compensation device 71 always becomes conjugate with a point (such as the pupil center) of the pupil, allowing stable wavefront compensation.

The eye-anterior-part illumination light source 45 illuminates an eye anterior part of the eye under measurement 60. For example, a Placido's ring or a keratoring may be used to project a predetermined pattern on the eye anterior part. When a keratoring is used, a pattern just around the center of curvature of the cornea is obtained by a keratoimage. The wavelength of light emitted from the eye-anterior-part illumination light source 45 is, for example, different from the first wavelength (860 nm or 780 nm in this case), and can be a long wavelength (such as 940 nm).

The eye-anterior-part observation system 4 includes a condenser lens and an eye-anterior-part image sensor 41, and guides a light beam emitted from the eye-anterior-part illumination light source 45 and reflected by and returned from the cornea 62 of the eye under measurement 60, to the eye-anterior-part image sensor 41. As a light source section, an appropriate light source for illuminating the eye under measurement 60 may be used instead of the eye-anterior-part illumination light source 45. The eye-anterior-part observation system 4 can also guide a light beam reflected by and returned from the eye anterior part or the cornea 62 of the eye under measurement 60 when an appropriate pattern (such as a Placido's ring) is projected on the eye under measurement 60, to the eye-interior-part image sensor 41. The eye-anterior-part image sensor 41 can obtain an eye-anterior-part image. The eye-anterior-part observation system 4 can also be used for alignment. The wavelength of light used for alignment can be a long wavelength (such as 940 nm) different, for example, from the first wavelength (780 nm in this case).

The third illumination optical system (fixation system) 5 includes, for example, an optical path for projecting an eye-sight-target for making the eye under measurement 60 have fixation or clouding and fogging, and is provided with a third light source section (such as a lamp) 51, a fixation target 52, and a relay lens. The system 5 can project the fixation target 52 on the retina 61 with a light beam emitted from the third light source section 51, and makes the eye under measurement 60 observe its image.

The wavefront-compensation-device control apparatus 15 deforms the wavefront compensation device 71 according to the output of the calculation apparatus 14-1. For example, the wavefront-compensation-device control apparatus 15 generates a control signal (such as a voltage) for deforming each element of the wavefront compensation device 71, based on wavefront aberration measured by the calculation apparatus 14-1 or based on compensation obtained by the calculation apparatus 14-1, and outputs the generated control signal to the wavefront compensation device 71 to compensate the wavefront.

The calculation apparatus 14-1 obtains optical characteristics that include higher-order aberrations, of the eye under measurement 60 or of a light beam which was reflected by the eye under measurement 60 and of which aberrations have been compensated for by the compensation optical section 70, according to the output from the point image light-receiving section 13. The calculation apparatus 14-1 may receive, instead of the output from the point image light-receiving section 13, wavefront measurement data that indicates at least the wavefront aberration of the eye under measurement 60 to obtain the optical characteristics. The calculation apparatus 14-1 also determines the amount of compensation for the wavefront compensation device according to the obtained optical characteristics and outputs the amount of compensation to the wavefront-compensation-device control apparatus 15.

The pupil-movement-distance calculation section 14-2 measures the displacement of the eye under measurement (such as the movement distance of the pupil) from the eye-anterior-part image generated by the eye-anterior-part image sensor 41. The pupil-movement-distance calculation section 14-2 can measure the movement distance of the center of the pupil as the displacement of the eye under measurement, but it may also obtain the movement distance of an appropriate position of the eye under measurement, such as the vertex of the cornea. The fundus-image generation section 14-3 obtains a fundus-image generated by the second light-receiving section 32, and displays or outputs the fundus-image.

Conjugate Relationship

The retina 61 of the eye under measurement 60, the fixation target 52 in the fixation system 5, the first light source section 17, and the point image light-receiving section 13 are conjugate. The pupil (iris) of the eye under measurement 60, the conversion member (Hartman plate) of the first light-receiving optical system 12, the aperture diaphragms 23-1, 23-2 and the cornea reflection removing mirror 33 are conjugate. The rotating diffusion plate 24 is conjugate with the pupil (an image is formed in the pupil), and can uniformly illuminate the whole of most of the retina 61.

Alignment Adjustment

Alignment adjustment will next be described. Alignment adjustment can be performed, for example, by the eye-anterior-part observation system 4.

Since, an image of the eye under measurement 60 is formed on the eye-anterior-part image sensor 41 by the eye-anterior-part illumination light source 45 (light source section), which illuminates the cornea 62 of the eye under measurement 60, alignment adjustment needs to be performed such that the center of the pupil matches the optical axis by using the image of the eye under measurement 60.

When a light source for illuminating the eye under measurement 60 by parallel light beams through the condenser lens, the beam splitter, and the afocal lens 81 is added to the eye-anterior-part observation system 4, light beams reflected by the cornea 62 of the eye under measurement 60 are returned as if they were diverging from a point positioned at half the radius of curvature of the cornea 62. The diverging light beams pass through the afocal lens 81, the beam splitter, and the condenser lens, and the eye-anterior-part image sensor 41 receives the light beams as a spot image. If the spot image on the eye-anterior-part image sensor 41 is not on the optical axis, the retina observation apparatus is moved up and down and from side to side so that the spot image is on the optical axis. When the spot image is brought onto the optical axis, alignment adjustment is completed.

3. Construction of Electrical System

Figure 2:
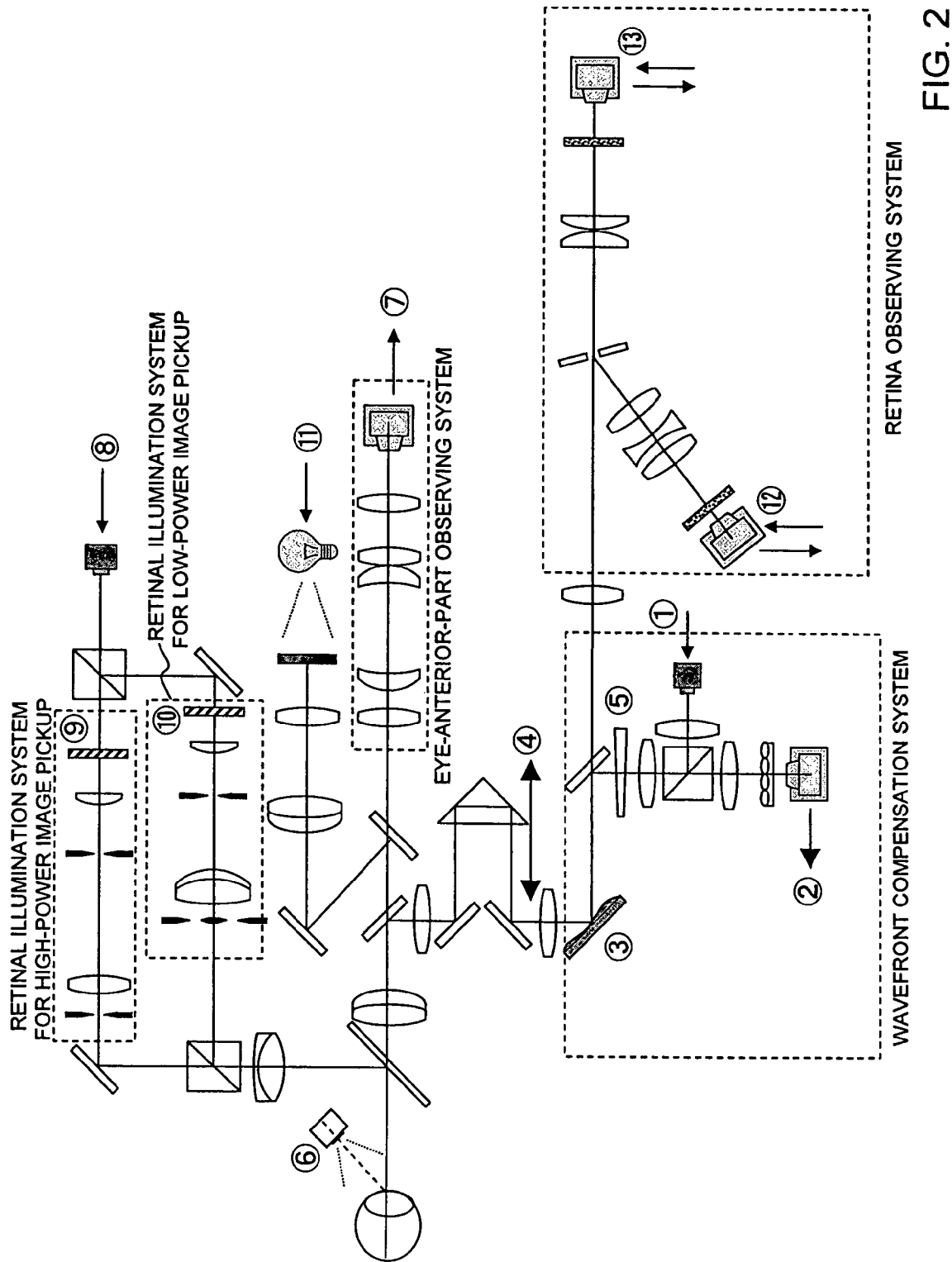
FIG. 2 is a diagram showing signals of this embodiment.
Figure 3:
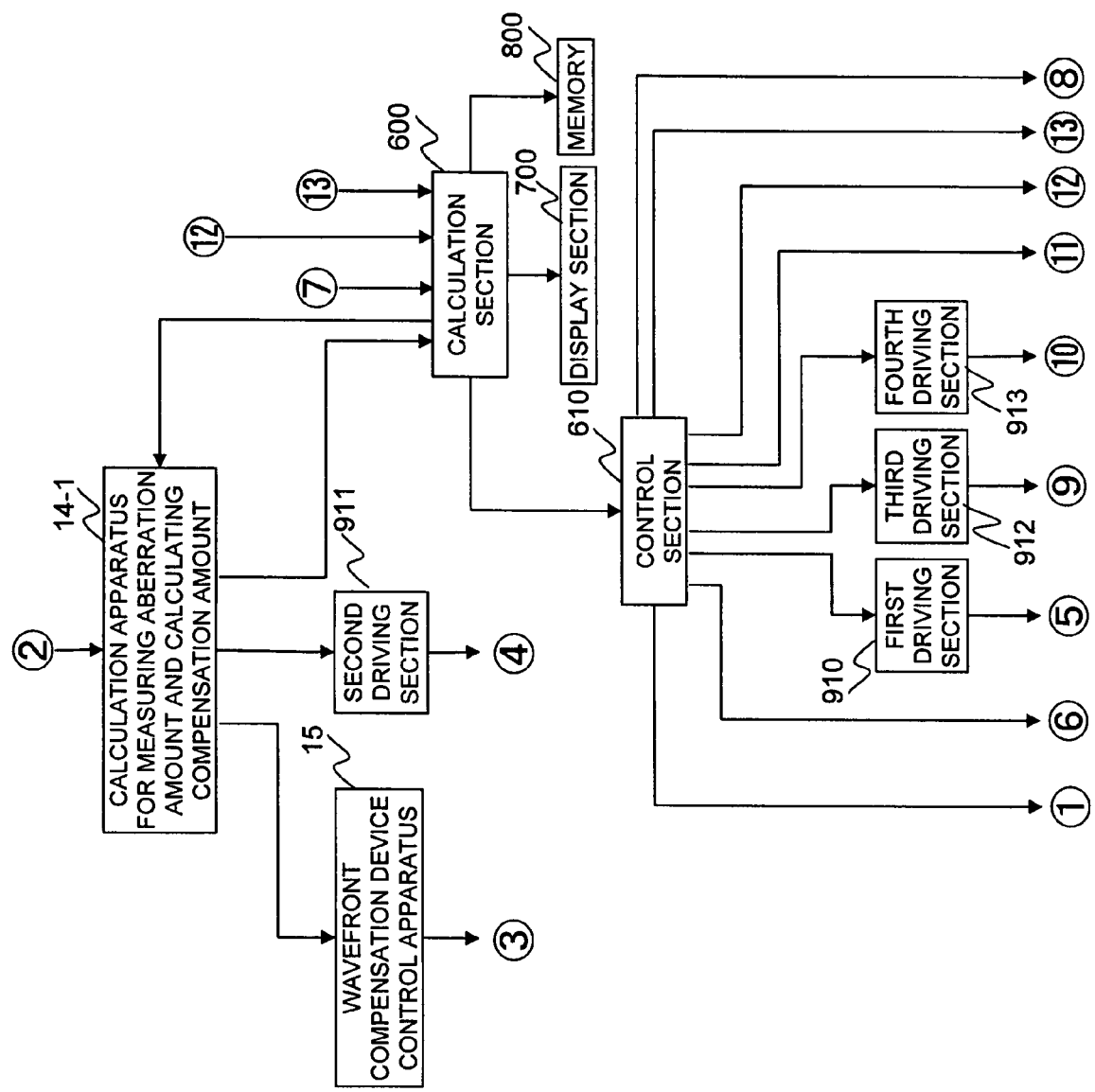
FIG. 3 is a block diagram showing an electrical system of this embodiment.

FIG. 3 is a block diagram showing the electrical system of the ophthalmologic imaging apparatus FIG. 2 is a diagram showing the signal of the ophthalmologic imaging apparatus.

The electrical system of the ophthalmologic imaging apparatus has a calculation section 600, a control section 610, a display section 700, a memory 800, a first driving section 910, a second driving section 911, a third driving section 912, and a fourth driving section 913. The ophthalmologic imaging apparatus may be further equipped with an input section. The input section maybe equipped with a pointing device for indicating proper buttons, icons, positions, areas, etc. displayed on the display section 700, a keyboard for inputting various kinds of data, etc.

The calculation section 600 contains a pupil-movement-distance calculation section 14-2, an image pickup device calculating/control device 14-3, for example. It may further contain a calculation apparatus 14-1. To the calculating section 600 are input a signal (12) from the high-power retinal image pickup device 32-2, a signal (13) from the low-power retinal image pickup device 32-1, a signal (7) from the eye-anterior-part observation system 4, and a signal from the calculation apparatus 14-1.

The calculation section 600 is supplied with the signal (7) from the eye-anterior-part observing system 4, and adjusts alignment, etc., for example. The calculation section 600 properly outputs the signals corresponding to these processing or other signals/data to the controller 610 for controlling the electrical driving system, the display section 700, the memory 800 and the calculation apparatus 14-1.

The control section 610 controls turn-on/turn-out of the illumination light source 21, the first light source section 17, the third light source section 51 and the eye-anterior-part illumination light source 45 and controls the first driving section 910, the third driving section 912, the fourth driving section 913, etc. on the basis of the control signals from the calculation section 600. The control section 610 outputs a signal (1) to the first light source section 17, outputs a signal (6) to the eye-anterior-part illumination light source 45, outputs a signal (11) to the third light source section 51, outputs the signal (12) to the high-power retinal image pickup device 32-2, outputs the signal (13) to the low-power retinal image pickup device 32-1, and outputs the signals to the first driving section 910, the third driving section 912 and the fourth driving section 913 on the basis of the signals corresponding to the calculation results in the calculation section 600. Furthermore, the control section 610 outputs a signal (8) to the illumination light source 21.

The aberration-measurement and compensation-computation calculation apparatus 14-1 receives a first signal (2) from the point image light-receiving section 13. According to the received signal, the calculation apparatus 14-1 calculates optical characteristics of the eye under measurement 60, such as aberrations and the amount of aberrations, and the amount of compensation used by the wavefront compensation device 71 for compensation. The calculation apparatus 14-1 outputs signals corresponding to these calculation results, or other signals and data to the calculation section 600, the wavefront-compensation-device control apparatus 15, and the second driving section 911, if necessary. The calculation apparatus 14-1 may be included in the calculation section 600. A signal may be input to the second driving section 911 through the control section 610.

The wavefront-compensation-device control apparatus 15 outputs a signal (3) according to the signal received from the calculation apparatus 14-1 to control the wavefront compensation device 17 so as to compensate for aberrations.

The display section 700 displays an image pickup result (retinal image or the like). The memory 800 properly stores measured aberration, pickup images, time, etc., the preset number N of images to be achieved, set values such as the exposure time of the image pickup device, etc. as occasion demands. The calculation section 600 properly reads out data from the memory 800 and writes data into the memory 800.

The first driving section 910 outputs a signal (5) at least during operation of a retinal image sensor 32 to rotate a rotary prism 16. The second driving section 911 outputs a signal (4)

to drive moving means of a moving prism 72, thereby moving the moving prism 72 in the optical axis direction. The third driving section 912 outputs a signal (9) to rotate the rotational diffusion plate of the retina illumination system for high-power image pickup 2-1 at a high speed. The fourth driving section 913 outputs a signal (10) to rotate the rotational diffusion plate of the retina illumination system for low-power image pickup 2-2 at a high speed.

4. Aberration Measurement

Next, an aberration measurement (a Zernike analysis) will be described. A generally known method of calculating Zernike coefficients $C_i^{2j-i}$ from Zernike polynomials will be described. The Zernike coefficients $C_i^{2j-i}$ are important parameters for grasping the optical characteristic of the subject eye 60 on the basis of inclination angles of the light fluxes obtained by the point image light-receiving section 13 through the conversion member, for example Hartmann plate.

Wavefront aberrations W (X, Y) of the subject eye 60 are expressed using the Zernike coefficients $C_i^{2j-i}$ and the Zernike polynomials $Z_i^{2j-i}$ by the following expression.

$$W(X, Y) = \sum_{i=0}^{n} \sum_{j=0}^{i} c_i^{2j-i} Z_i^{2j-i}(X, Y)$$

Where, (X, Y) denotes vertical and horizontal coordinates of the Hartmann plate.

Besides, with respect to the wavefront aberrations W(X, Y), when the horizontal and vertical coordinates of the point image light-receiving section 13 are denoted by (x, y), a distance between the Hartmann plate and the point image light-receiving section 13 is denoted by f, and a movement distance of a point image received by the point image light-receiving section 13 is denoted by ($\Delta$x, $\Delta$y), the following expression is established.

$$\frac{\partial W(X, Y)}{\partial X} = \frac{\Delta x}{f}$$

$$\frac{\partial W(X, Y)}{\partial Y} = \frac{\Delta y}{f}$$

Where, the Zernike polynomials $Z_i^{2j-i}$ are expressed by the following numerical expressions. (More specifically expressions, for example, see JP-A-2002-209854.)

$$Z_n^m = R_n^m(r) \left\{ \frac{\sin}{\cos} \right\} \{m\theta\}$$

$$m > 0 \quad \sin$$
$$m \leq 0 \quad \cos$$

$$R_n^m(r) = \sum_{S=0}^{(n-m)/2} (-1)^S \frac{(n-S)!}{S!\left\{\frac{1}{2}(n-m)-S\right\}!\left\{\frac{1}{2}(n+m)-S\right\}!} r^m$$

Incidentally, with respect to the Zernike coefficients $C_i^{2j-i}$, specific values can be obtained by minimizing the squared error expressed by the following numerical expression.

$$S(x) = \sum_{i=1}^{data\ number} \left[ \left\{ \frac{\partial W(X_i, Y_i)}{\partial X} - \frac{\Delta x_i}{f} \right\}^2 + \left\{ \frac{\partial W(X_i, Y_i)}{\partial Y} - \frac{\Delta y_i}{f} \right\}^2 \right]$$

Where, W(X, Y): wavefront aberrations, (X, Y): Hartmann plate coordinates, ($\Delta$x, $\Delta$y): a movement distance of a point image received by the point image light-receiving section 13, f: a distance between the Hartmann plate and the point image light-receiving section 13.

The calculation apparatus 14-1 calculates the Zernike coefficients $C_i^{2j-i}$, and uses this to obtain eye optical characteristics such as spherical aberrations, coma aberrations, and astigmatism aberrations. The calculation apparatus 14-1 calculates aberration quantities $RMS_i^{2j-i}$ using the Zernike coefficients $C_i^{2j-i}$ by the following numerical expression.

$$RMS_i^{2j-i} = \sqrt{\frac{\varepsilon_i^{2j-i}}{2(i+1)}} \; c_i^{2j-i}$$

$$\left(\varepsilon_i^{2j-i} = 2(2j = i),\; \varepsilon_i^{2j-i} = 1(2j \neq i)\right)$$

5. Perforated Mirror

Figure 4A:
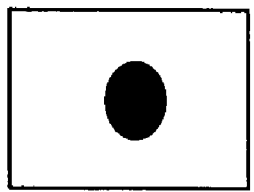
FIGS. 4A to 4C are diagrams showing a cornea reflection removing mirror (perforated mirror) 33.
Figure 4B:
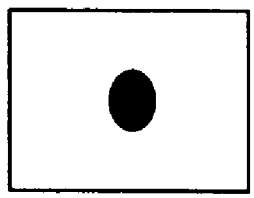
Figure 4C:
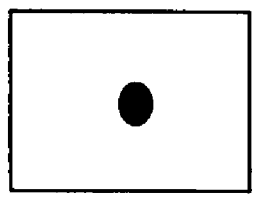

FIGS. 4A to 4C are diagrams showing the cornea reflection removing mirror (perforated mirror) 33.

For example, FIG. 4A shows a perforated mirror for observing a cell, FIG. 4B shows a perforated mirror for observing a leucocyte, and FIG. 4C shows a perforated mirror for observing a blood vessel.

As shown in FIGS. 4A to 4C, a hole (aperture) corresponding to the size of the aperture diaphragm is formed at the center portion of the perforated mirror 33. The size of the hole may be varied in accordance with desired resolution. The perforated mirror 33 is located so as to be conjugated with the pupil.

In a case where a portion spaced from the center of the pupil by $\phi$h [mm] is used as a low-power system when the magnification of the pupil is represented by $\alpha$, the diameter of the hole is represented by $\alpha \times$h [mm]. In general, the mirror 33 is disposed while tilted, and thus the hole is frequently designed to have an elliptical shape as shown in FIGS. 4A to 4C.

Figure 5B:
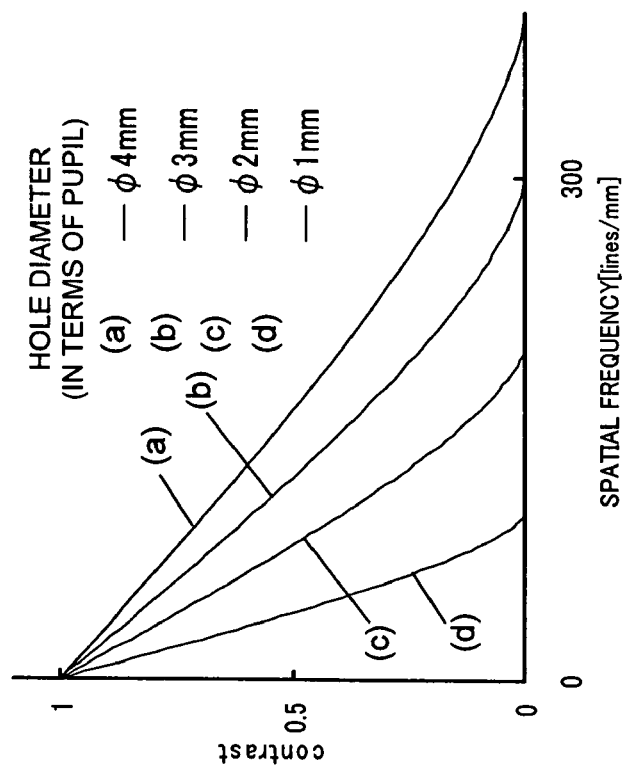
FIGS. 5A and 5B are diagrams showing variation of MTF in accordance with the diameter of the perforated mirror 33.
Figure 5A:
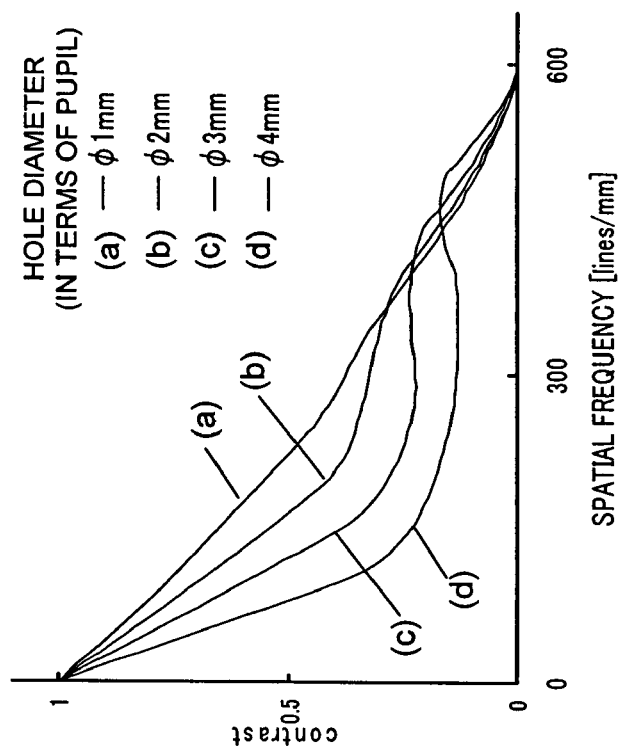

FIGS. 5A and 5B are diagrams showing variation of MTF (Modulation Transfer Function) of the optical system in accordance with the diameter of the perforated mirror 33.

FIG. 5A is a diagram showing variation of MTF (Contrast) of the high-power retina observing system 31-2 (mirror reflection light) in accordance with the diameter of the perforated mirror 33. FIG. 5B is a diagram showing variation of MTF of the low-power retina observing system 31-1 (light passing through the hole) in accordance with the diameter of the perforated mirror 33.

The light reflected from the cornea reflection removing mirror 33 of the optical system is focused to the image pickup device (CCD) 32-2 of the high-power retina observing system 31-2, and light passing through the hole of the cornea reflection removing mirror 33 passes through the low-power retina observing system 31-1 and is focused to the image pickup device (CCD) 32-1 of the low-power system.

The value of the spatial frequency is determined by the size of a target object to be observed. For example, if the size of the target object to be observed is equal to about 2 μm, the spatial frequency is equal to about 300 [lines/mm], if the size of the target object is equal to about 10 μm, the spatial frequency is equal to about 60 [lines/mm], and if the size of the target object is equal to about 30 μm, the spatial frequency is equal to about 20 [lines/mm].

The value of the contrast is estimated to corresponds to the ratio between a signal existing portion and a signal non-existing portion, and actually, even when the contrast value of a target object is equal to 0.1, the target object can be separated. If it is like an image, the target object can be minutely observed with no image processing if the contrast is equal to about 0.3. As example of this embodiment, the contrast is set to 0.3, however, it may be set to other values.

In the two graphs of FIGS. 5A and 5B, the graph of FIG. 5A is a graph of a light image reflected from the cornea reflection removing mirror 33, and FIG. 5B is a graph of a light image passing through the hole of the cornea reflection removing mirror 33. As shown in FIG. 5A, when the target object is minute (for example, 2 μm or the like), the diameter of the hole is as small as possible. However, in that case, the image quality of the low magnification is deteriorated as shown in FIG. 5B. In this embodiment, the optimal hole diameter can be selected in accordance with an object to be taken (observation target).

For example, when the pupil diameter is equal to φ6 mm and a cell-level resolution (about 2 μm) is desired, in order to perform high-power observation with reflected light, it is sufficient that the spatial frequency in FIG. 5A is equal to 300 [lines/mm] and the contrast is equal to about 0.3, and it is desired that the diameter of the hole is not more than φ2 mm in terms of the pupil.

On the other hand, in the low-power optical system 31-1, sufficient resolution can be achieved to resolve a rough portion such as a blood vessel or the like even if the hole diameter is equal to φ1 mm. However, the light amount is small and thus S/N (Signal-to-Noise ratio) is worse. As shown in FIG. 5B, the contrast in the case of φ1 mm is lower than the contrast in the case of φ2 mm, and the image quality is lowered. Accordingly, for example, φ2 mm can be selected. Likewise, the perforated mirror may be exchanged in accordance with the observation target by selecting a leucocyte level (about 10 μm), a blood vessel level (about 30 μm) or the like. As described above, the hole diameter of the cornea reflection removing mirror 33 can be determined in consideration of both the contrast of the high-power system and the contrast of the low-power system.

If the high-power system having a contrast value of about 0.1 is selected and an image is subjected to image processing, an observable high-power image could be achieved. For example, if the size of the target object is equal to 2 μm, the spatial frequency is set to 300 [lines/mm] and the contrast is set to 0.1, whereby the hole diameter of φ4 mm can be used. In this case, as compared with the case where the contrast of 0.3 is selected, a higher quality low-power image can be achieved.

6. Operation

Figure 6:
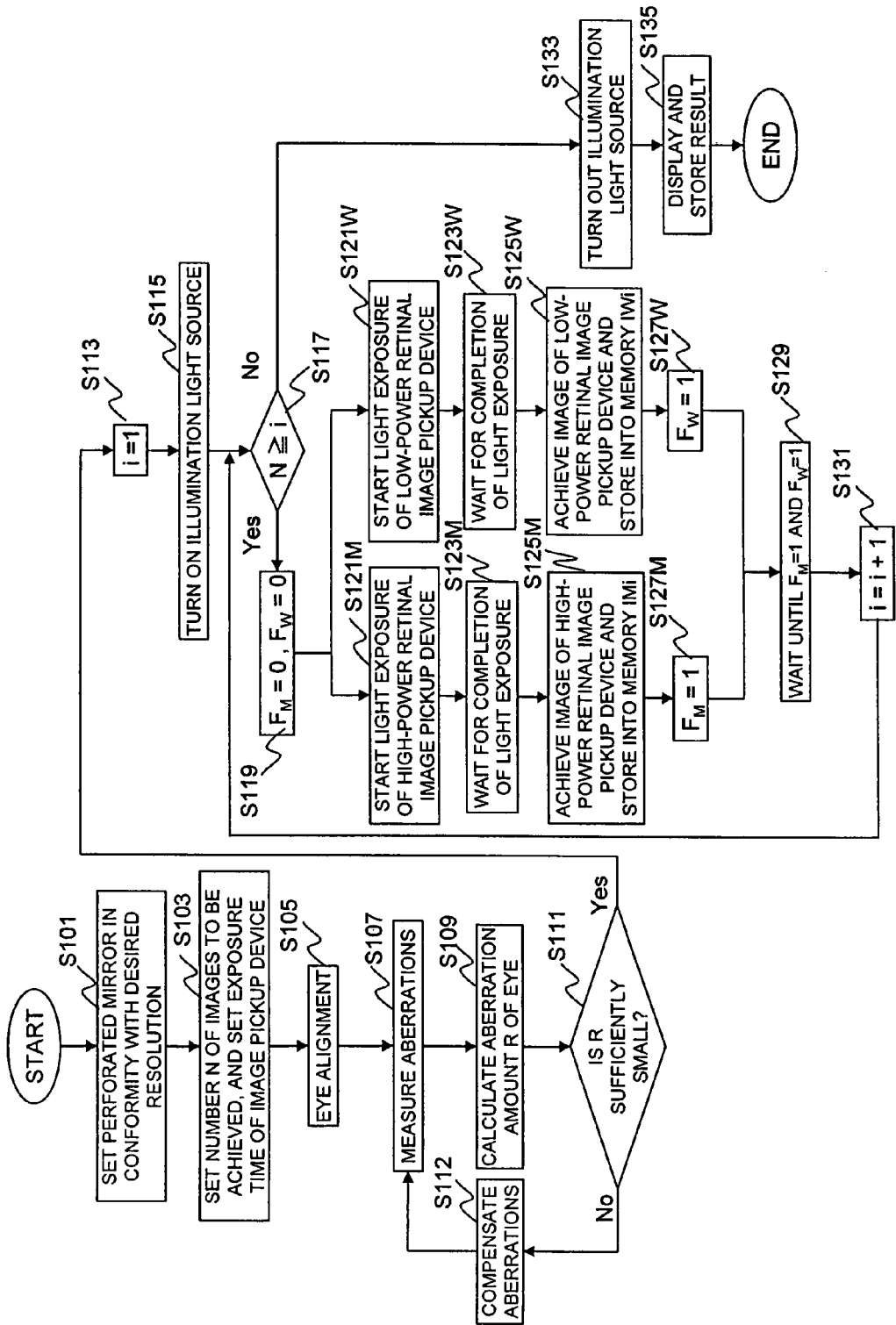
FIG. 6 is an overall flowchart showing the embodiment.

FIG. 6 is an overall flowchart of this embodiment.

First, a perforated mirror 33 which is matched with desired resolution is disposed (S101). For example one of plural perforated mirrors 33 which are prepared in advance may be inserted into the retina observing system 3. Furthermore, the calculation section 600 may select one of the plural prepared perforated mirrors 33 by an input from the input section. Subsequently, the number N of images to be achieved and the exposure time of each of the high-power retinal image pickup device 32-2 and the low-power retinal image pickup device 32-1 are set (S103) by the calculation section 600. The number N of the images to be achieved and the exposure time of each of the high-power retinal image pickup device 32-2 and the low-power retinal image pickup device 32-1 may be input from a proper input device or the like, or values stored in the memory 800 in advance may be read out.

Subsequently, the calculation section 600 carries out alignment of eye (S105). A spot for alignment by another light source may be used for the alignment of eye. In this embodiment, for example, a flux of reflection light of a light flux projected to the anterior eye is incident to the eye-anterior-part image sensor 41, and the overall apparatus or the eye is moved by an operator so that the center of the anterior eye is located at the original point of the eye-anterior-part image sensor 41, whereby the eye alignment can be performed. The eye alignment may be performed at a suitable timing.

The calculation apparatus 14-1 carries out aberration measurement of the eye (eye ball) under measurement (S107). Subsequently, the calculation apparatus 14-1 calculates the aberration amount R of the eye (S109). For example, the calculation apparatus 14-1 calculates the aberration amount R of the eye on the basis of the measurement result (for example, the Zernike coefficient $C_i^{2j-i}$) of the aberration measurement achieved in step S107, and stores the calculation result in the memory 800. The aberration amount R can be calculated as a standard deviation from the ideal wavefront (non-aberration) of the measurement result, however, it can be easily calculated by using the Zernike coefficient according to the following equation. Order in the equation represents the order of the Zernike coefficient, and for example, it is set like order=4 or order=6.

$$R = \sqrt{\sum_{i=0}^{order} \sum_{j=0}^{i} \frac{\varepsilon_i^{2j-i}}{2(i+1)} (c_i^{2j-i})^2}$$

$$(\varepsilon_i^{2j-i} = 2(2j = i), \varepsilon_i^{2j-i} = 1(2j \neq i))$$

Subsequently, the calculation apparatus 14-1 judges whether the aberration amount R is sufficiently small or not (S111). For example, it judges whether the aberration amount R is smaller than a predetermined threshold value or not. If the aberration amount R is not sufficiently small (S111), the calculation apparatus 14-1 executes aberration compensation processing (S112). For example, the calculation apparatus 14-1 moves the moving prism 72 through the second driving section 911, and controls the wavefront compensation device 71 through the wavefront compensation device control apparatus 15, whereby the aberration is compensated so as to offset the measured aberration. Thereafter, the processing returns to step S107.

On the other hand, if the aberration amount R is sufficiently small (S111), the calculation section 600 executes initialization (S113). For example, the calculation section 600 sets a parameter i to i=1. Here, i represents an image achieving frequency or image pickup frequency. The calculation section 600 turns on the illumination light source 21 by the control section 610 (S115).

Subsequently, the calculation section 600 judges whether the parameter i is not more than N (S117). That is, it judges whether images of N are achieved or not. The calculation section 600 initializes the flag if the parameter i is not more than N (S117) (S119). For example, the calculation section 600 sets the flag $F_M$ to $F_M=0$ and sets the flag $F_W$ to $F_W=0$. For example, the flag $F_M$ of this embodiment is a flag for judging the state of the-high-power retinal image pickup device 32-2, and it is set so that "1" represents completion of achievement of a retinal image, and "0" represents incompletion of achievement of retinal image. Furthermore, the flag $F_W$ is a flag for judging the state of the low-power retinal image pickup device 32-1, and it is set so that "1" represents completion of achievement of a retinal image, and "0" represents incompletion of achievement of a retinal image. The setting of the flags is not limited to the above mode, and other setting may be properly used.

Subsequently, the calculation section 600 executes the processing of achieving a high-power retinal image (step S121M to step S127M) and the processing of achieving a low-power retinal image (step S121W to step S127W) in parallel. In the processing of achieving the high-power retinal image, the calculation section 600 starts light exposure of the high-power retinal image pickup device 32-2 by the control section 610 (S121M). The calculation section 600 waits for completion of the light exposure of the high-power retinal image pickup device 32-2 (S123M). For example, it waits for the exposure time set in step S103. If the light exposure of the high-power retinal image pickup device 32-2 is finished in step S123M, the calculation section 600 reads out image data from the high-power retinal image pickup device 32-2, and stores the data as the image data IMi corresponding to the parameter i into the memory 800 (S125M). Furthermore, the calculation section 600 sets the flag $F_M$ to $F_M=1$ (S127M), and shifts the processing to step S129.

In the processing of achieving the low-power retinal image, the calculation section 600 starts the light exposure of the low-power retinal image pickup device 32-1 (S121W) by the control section 610. The calculation section 600 waits for completion of the light exposure of the low-power retinal image pickup device 32-1 (S123W). When the light exposure of the low-power retinal image pickup device 32-1 is finished in step S123W, the calculation section 600 reads out image data from the low-power retinal image pickup device 32-1, and stores the data as the image data IWi corresponding to the parameter i into the memory 800 (S125W). Furthermore, the calculation section 600 sets the flag $F_W$ to $F_W=1$ (S127W), and shifts the processing to step S129.

The calculation section 600 waits until the flag $F_M$ is set to $F_M=1$ and the flag $F_W$ is set to $F_W=1$ (S129). That is, it waits until both the high-power image and the low-power image are stored in the memory. If the calculation section 600 judges in step S129 that $F_M=1$ and $F_W=1$ (step S129), the value of i is added (for example, i=i+1) (S131), and the calculation section 600 returns the processing to step S117.

As described above, the calculation section 600 repetitively executes the processing of steps S117 to S131. When a predetermined number of images are achieved (S117: No), the calculation section 600 turns off the illumination light source 21 by the control section 610 (S133). The calculation section 600 displays the data of the high-power and low-power retinal images and the like achieved in the above processing on the display section 700 (S135). The calculation section 600 may store suitable data into the memory 800.

Figure 7:
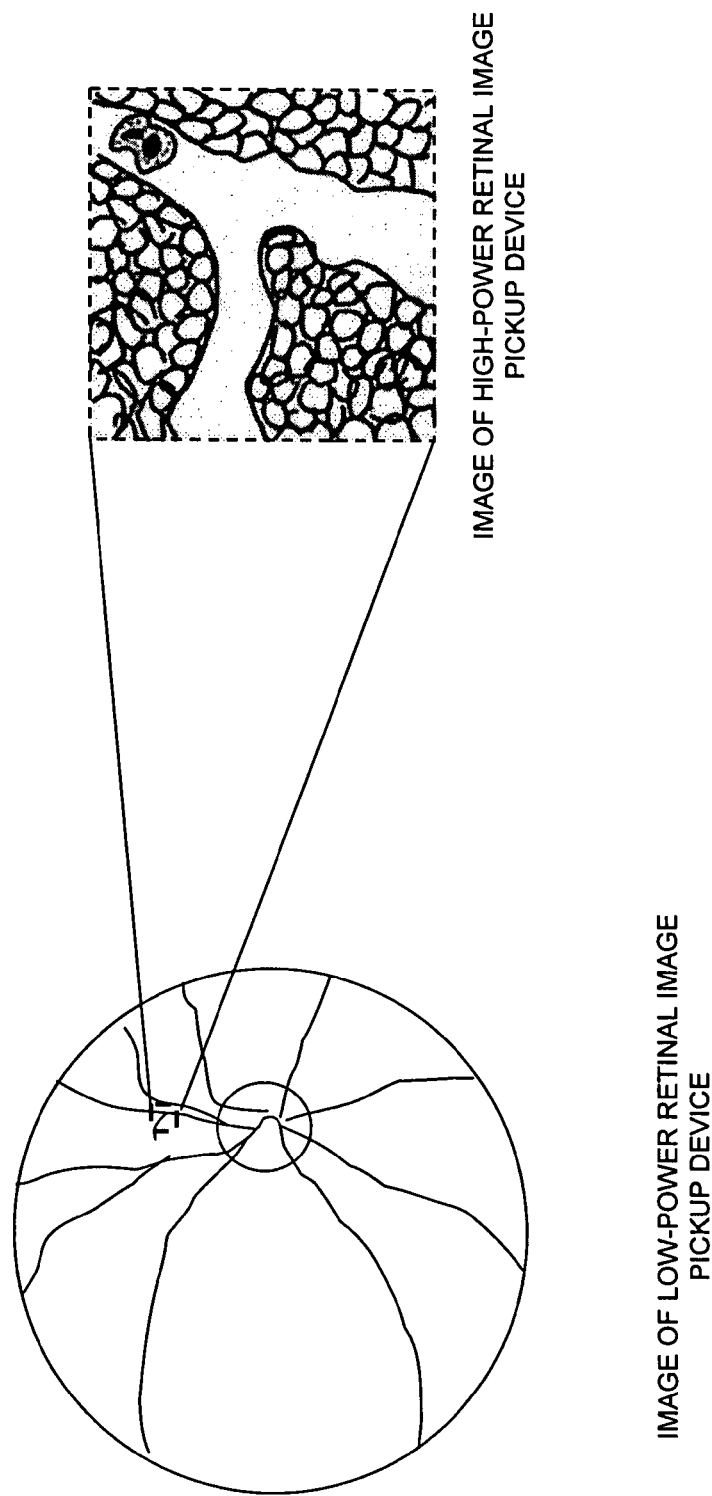
FIG. 7 is a diagram showing a display example of a result according to the embodiment.

FIG. 7 is a diagram showing a display example of the result of this embodiment.

FIG. 7 shows an example when the number N of achieved images is equal to 1. As shown in FIG. 7, a high-power image (right side in FIG. 7) in which a cell can be observed as shown in FIG. 7 and a broad-range image (left side in FIG. 7) can be observed and displayed at the same time. By moving a fixation target 52, the eye observing the fixation target 52 is moved, and a high-power image at a desired position may be achieved.

The present invention is applicable to an image pickup device for picking up a retinal image for the department of ophthalmology, for example.

What is claimed is:

1. An ophthalmologic imaging apparatus comprising:
a light source section for emitting illumination light to illuminate a retina;
an illumination optical system for illuminating the retina of an eye under measurement by a first passage for passing a part of an illumination light flux from the light source section through a first aperture diaphragm having an opening formed at a center portion at a conjugate position with a pupil, and a second passage for passing a part of the illumination light flux from the light source section through a second aperture diaphragm having an opening formed on a periphery portion at a conjugate position with the pupil;
an aberration compensation section for applying compensation to a reflection light flux from the retina on the basis of measured aberrations so as to offset the aberrations;
an aberration measuring section for illuminating the eye under measurement, receiving a reflection light flux under the illumination from the eye under measurement through the aberration compensation section and, measuring the aberrations of the reflection light flux;
an image pickup optical system including a reflection section that has an opening at a center portion at a conjugate position with the pupil, passes a light flux at the center portion and reflects the light flux at a peripheral portion, for achieving images of first and second magnifications of the retina of the eye under measurement by a third passage for achieving a retinal image of a first magnification by the reflection light flux which is from the retina and is compensated in aberrations in the aberration compensation section and is passed through the opening of the reflection section, and a fourth passage for achieving a retinal image of a second magnification by the reflection light flux which is from the retina and is compensated in aberrations in the aberration compensation section and is reflected from the peripheral portion around the opening of the reflection section;
a first light-receiving section for receiving the light flux passing through the third passage; and
a second light-receiving section for receiving the light flux passing through the fourth passage, and
images of different magnifications being achieved by the first light-receiving section and the second light receiving section.

2. The ophthalmologic imaging apparatus according to claim 1, wherein
the size of the opening of the reflection section is changeable in accordance with the difference of a desired observation target on the retina.

3. The ophthalmologic imaging apparatus according to claim 1, further comprising
a dividing section for dividing the illumination light flux from the light source section into a light flux of first polarization light and a light flux of second polarization light, leading the light flux of first polarization light to the first passage and leading the light flux of second polarization light to the second passage,
wherein the image pickup optical system
has, on the third passage, a first polarizer for passing the light flux of second polarization light out of the light fluxes which are passed through the reflection section and include the light flux of first polarization light reflected from a cornea and the light flux of second polarization light reflected from the retina, to lead the reflection light flux reflected from the retina to the first light-receiving section, and has, on the fourth passage, a second polarizer for passing the light flux of first polarization light out of the light fluxes which are reflected from the reflection section and include the light flux of second polarization light reflected from the cornea and the light flux of first polarization light reflected from the retina, to lead the reflection light flux reflected from the retina to the second light-receiving section.

4. The ophthalmologic imaging apparatus according to claim 3, wherein the first polarization light and the second polarization light are P-polarization light and S-polarization light, respectively.

5. The ophthalmologic imaging apparatus according to claim 1, wherein the image pickup optical system has an optical system having first magnifying power on the third passage, and an optical system having second magnifying power on the fourth passage, the second magnifying power is higher than the first magnifying power.

6. The ophthalmologic imaging apparatus according to claim 1, further comprising a display section for displaying the retinal image of the first magnification based on the first light-receiving section and the retinal image of the second magnification based on the second light-receiving section.

* * * * *